United States Patent [19]

Caron et al.

[11] Patent Number: 4,837,213

[45] Date of Patent: Jun. 6, 1989

[54] PHARMACEUTICAL VEHICLE FOR ACTIVE SUBSTANCES IN THE FORM OF AN ANHYDROUS GEL

[75] Inventors: Daniele Caron, Valbonne; Braham Shroot, Antibes, both of France

[73] Assignee: Centre Internatinal de Recherches Dermatologiques C.I.R.D., Valbonne, France

[21] Appl. No.: 117,413

[22] Filed: Nov. 2, 1987

Related U.S. Application Data

[63] Continuation of Ser. No. 778,066, Sep. 20, 1985, abandoned.

[30] Foreign Application Priority Data

Sep. 21, 1984 [FR] France ........................... 84 14512

[51] Int. Cl.$^4$ .................. A61K 31/56; A61K 31/695
[52] U.S. Cl. .............................. 514/179; 514/63; 514/944; 514/559; 514/680
[58] Field of Search .................. 514/63, 559, 179, 680

[56] References Cited

U.S. PATENT DOCUMENTS

| | | | |
|---|---|---|---|
| 3,185,627 | 5/1965 | Kass ........................................ | 514/63 |
| 3,880,996 | 4/1975 | Fisher ...................................... | 514/63 |
| 3,946,106 | 3/1976 | Chien et al. ........................... | 424/15 |
| 3,992,518 | 11/1976 | Chien et al. ........................... | 424/22 |
| 4,472,374 | 9/1984 | Dowrick et al. ...................... | 424/78 |
| 4,495,203 | 1/1985 | Grollier et al. ....................... | 424/365 |
| 4,513,011 | 4/1985 | Grollier et al. ....................... | 514/730 |

FOREIGN PATENT DOCUMENTS

0076068 4/1983 European Pat. Off. .
2107588 5/1983 United Kingdom .

*Primary Examiner*—Leonard Schenkman
*Assistant Examiner*—Joseph A. Lipovsky
*Attorney, Agent, or Firm*—Oliff & Berridge

[57] ABSTRACT

A pharmaceutical vehicle used for administering and protecting active substances, in the form of an anhydrous gel and having a viscosity of at least 540 cps, comprising paraffin oil, at least one fatty acid alkyl ester and a polyvinyldimethyl siloxane-type elastomeric silicone, used as a thickener.

9 Claims, No Drawings

PHARMACEUTICAL VEHICLE FOR ACTIVE SUBSTANCES IN THE FORM OF AN ANHYDROUS GEL

This is a continuation of application Ser. No. 778,066 filed Sept. 20, 1985 now abandoned.

BACKGROUND OF THE INVENTION

This invention involves a new pharmaceutical vehicle for active substances in the form of an anhydrous gel, namely for substances which are sensitive to oxidation.

Many active substances which are sensitive to oxidation caused by oxygen in the air are used in the treatment of dermatological conditions. Specific examples of these active substances include but are not limited to anthralin (also called dithranol) and its derivatives idoxuridine, tretinoin, etc.

Among these substances, the compound anthralin is particularly active in the treatment of psoriasis, but disadvantageously, is very easily degraded by oxygen, subsequently forming dark-colored quinones or polymers which can stain the skin as well as clothing.

Various mixtures for processing and administering unstable or easily oxidized substances such as anthralin are already known. In connection therewith, Belgian Pat. No. 894,778 teaches the use of thickened mixtures comprising at least one fatty acid alkyl ester, wherein the fatty acid contains 12 to 18 carbon atoms and the alkyl group, with or without a branched chain, has 2 or 3 carbon atoms, and at least one thickening agent selected from the silica group with a particle size under 30 μM and polyethylene powders whose volumetric mass is between 0.90 and 0.96 (g/cm$^3$).

The mixtures involved in the above-mentioned Belgian patent, although enabling anthralin and its derivatives to be stabilized, are not conducive to adequate penetration by the anthralin, thus causing the anthralin to concentrate in the upper layers of the skin, when the mixture is applied thereto.

Furthermore, the mixtures must be of a sufficient viscosity to prevent the product from dripping onto healthy skin and potentially irritating it. Even is mixtures using silicas or polyethylene-type resins as thickeners are sufficiently viscous, they are difficult to eliminate, which constitutes another drawback in addition to the fact that such mixtures do not always penetrate sufficiently.

SUMMARY OF THE INVENTION

This invention involves a new pharmaceutical vehicle in the form of an anhydrous gel which not only allows good preservation of unstable, oxidizable substances, but also makes these active substances readily available.

An object of the invention is to offer a new pharmaceutical product, a pharmaceutical vehicle for active substances. This vehicle is an anhydrous gel whose viscosity is at least 540 cps (CONTRAVES) and which comprises essentially paraffin oil, at least one fatty acid alkyl ester and polyvinyldimethyl siloxane-type elastomeric silicone used as a thickener.

DETAILED DESCRIPTION

The vehicle of the invention is an anhydrous gel, having a viscosity at least 540 cps and comprising liquid paraffin oil, at least one fatty acid alkyl ester, and a polyvinyldimethyl siloxane-type elastomeric silicone. Test have shown the importance of the choice of these three principal substances for the gel involved in this invention.

For example, when attempts have been made to replace the paraffin oil by other oily substances or to substitute other substances for the polyvinyldimethyl siloxane-type elastomeric silicone, the following undesirable results have been noted: a lack of stability in the mixtures; and/or a pronounced decrease in the penetrability of the active compounds; and/or a viscosity which does not satisfy the requirements.

The pharmaceutical vehicle of the present invention can thus be used not only with easily oxidizable substances such as anthralin, but also with other substances whose activity would be enhanced by good penetration. In this respect, the new vehicle of the invention is particularly suited to active substances whose activity is localized; for example, certain antiinflammatories such as hydrocortisone and products used to treat acne, such as retinoids.

According to the invention, the thickener used for the anhydrous gel consists of polyvinyldimethyl siloxane-type elastomeric silicone combined with a resin binder of silica.

The elastomeric silicones in the pharmaceutical vehicle of the present invention can be expressed by the following formula:

$$X-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_n-\underset{\underset{CH_3}{|}}{\overset{\overset{CH_3}{|}}{Si}}-X$$

wherein:

X represents —OH and n is such that the viscosity of the elastomeric silicone combined with the silica resin binder is between about 410 and 480 ps measured at 24° C. (CONTRAVES).

This thickener is nicely compatible with the gel's two other ingredients and, when mixed therewith, allows the desired viscosity to be attained. Such products are described in BSM 8424M.

Among the preferred elastomeric silicones is the product sold by the DOW CORNING CORPORATION under the trademark "DOW CORNING MDX-4-4210", which is marketed as a kit comprising a basic product (elastomeric silicone + silica) plus a crosslinking agent or a vulcanization catalyst. The basic product has a viscosity of about 450 ps (CONTRAVES), and is used solely as a thickening agent in this invention.

The fatty acid alkyl ester is an ester of a fatty acid having 12 to 18 carbon atoms, and a straight or branched chain alkyl group having 2 or 3 carbon atoms. The preferred fatty acid alkyl esters include isopropyl myristate, isopropyl palmitate, ethyl myristate and mixtures thereof.

The paraffin oil serves to reflect light, to facilitate penetration by the active ingredient and to give an attractive appearance to the gel.

In order to attain the required viscosity, the weight ratio between the elastomeric silicone and the fatty acid alkyl ester should preferably be in the range of 0.90 to 1.25.

According to one of the preferred embodiments the anhydrous gel pharmaceutical vehicle comprises:

0.5 to 2% paraffin oil by weight;
50±2.5% fatty acid alkyl ester(s) by weight; and
49±2.5% polyvinyldimethyl siloxane-type elastomeric silicone by weight.

The active substances to be administered by means of the anhydrous gel featured in the invention are generally present in concentrations ranging from 0.05 to 5%, such substances being soluble or partially soluble in the gel. The active substances administrable through the anhydrous gel of the present invention include but are not limited to anthralin, cis- and trans-retinoic acids, hydrocortisone and 17-α-hydrocortisone butyrate. The following examples are illustrative only, and it goes without saying that the pharmaceutical vehicle featured in the present invention is not limited to these substances, and where appropriate may be used for other active substances which can be enhanced by good preservation and good penetrability.

EXAMPLE 1

Anthralin-base gel

This gel is obtained by mixing the following ingredients:

| | |
|---|---|
| isopropyl myristate | 49.70 g |
| elastomeric silicone "DOW CORNING MDX-4-4210" (trademark) | 49.00 g |
| paraffin oil | 1.00 g |
| anthralin | 0.30 g |

EXAMPLE 2

All trans-retinoic acid-base gel

This gel is obtained by mixing the following ingredients:

| | |
|---|---|
| isopropyl myristate | 49.95 g |
| elastomeric silicone "DOW CORNING MDX-4-4210" (trademark) | 49.95 g |
| paraffin oil | 1.00 g |
| all-trans-retinoic acid | 0.05 g |

EXAMPLE 3

17-α-hydrocortisone butyrate-base gel

This gel is obtained by mixing the following ingredients:

| | |
|---|---|
| isopropyl palmitate | 49.90 g |
| elastomeric silicone "DOW CORNING MDX-4-4210" (trademark) | 49.00 g |
| paraffin oil | 1.00 g |
| 17-α-hydrocortisone butyrate | 0.10 g |

EXAMPLE 4

Hydrocortisone-base gel

This gel is obtained by mixing the following ingredients:

| | |
|---|---|
| isopropyl myristate | 49.90 g |
| elastomeric silicone "DOW CORNING MDX-4-4210" (trademark) | 49.00 g |
| paraffin oil | 1.00 g |
| hydrocortisone | 0.10 g |

What is claimed is:

1. A pharmaceutical vehicle comprising an anhydrous gel consisting of:
   0.5% to 2% by weight of paraffin oil;
   50±2.5% by weight of an alkyl ester of a fatty acid having 12 to 18 carbon atoms, the alkyl radical being straight or branched and having 2 or 3 carbon atoms; and
   49±2.5% by weight of a polyvinyldimethyl siloxane-type elastomeric silicone combined with a silica binder,
   said vehicle being of a sufficient viscosity to prevent it from dripping when applied to skin.

2. A pharmaceutical vehicle according to claim 1, wherein the polyvinyldimethyl siloxane-type elastomeric silicone, combined with the silica binder, has the following formula:

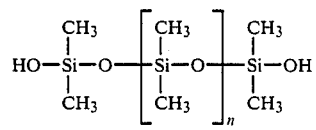

wherein n is selected such that the viscosity of the elastomeric silicone combined with the silica binder is between 410 and 480 ps measured at 24° C.

3. A pharmaceutical vehicle according to claim 1, wherein the fatty acid alkyl ester is selected from the group consisting of isopropyl myristate, isopropyl palmitate, ethyl myristate and mixtures thereof.

4. A pharmaceutical vehicle according to claim 1, wherein the weight ratio between the elastomeric silicone and the fatty acid alkyl ester is between 0.90 and 1.25.

5. A pharmaceutical vehicle comprising an anhydrous gel having a viscosity of at least 540 cps, said anhydrous gel consisting of:
   0.5 t0 2% by weight of paraffin oil;
   50±2.5% by weight of an alkyl ester of a fatty acid having 12 to 18 carbon atoms, the alkyl radical being straight or branched and having 2 or 3 carbon atoms, and
   49±2.5% by weight of a polyvinyldimethyl siloxane-type elastomeric silicone combined with a silica binder.

6. A pharmaceutical composition comprising a pharmaceutical vehicle in the form of an anhydrous gel and at least one topically dermatologically active pharmaceutical substance, said pharmaceutical vehicle consisting of:
   0.5% to 2% by weight of paraffin oil;
   50±2.5% by weight of an alkyl ester of a fatty acid having 12 to 18 carbon atoms, the alkyl radical being straight or branched and having 2 or 3 carbon atoms; and
   49±2.5% by weight of a polyvinyldimethyl siloxane-type elastomeric silicone combined with a silica binder,
   said vehicle being of a sufficient viscosity to prevent it from dripping when applied to skin.

7. A pharmaceutical composition according to claim 6, wherein said pharmaceutical substance is selected from the group consisting of anthralin, cis-retinoic acid, trans-retinoic acid, hydrocortisone and 17-α-hydrocortisone butyrate.

8. A pharmaceutical composition according to claim 7, wherein the pharmaceutical substance is present in a concentration ranging from 0.05 to 5% by weight of the total weight of the anhydrous gel.

9. A pharmaceutical composition according to claim 6, wherein the polyvinyldimethyl siloxane-type elastomeric silicone, combined with a silica binder, has the formula:

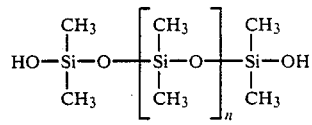

wherein n is selected such that the viscosity of the elastomeric silicone combined with the silica binder is between 410 and 480 ps measured at 24° C.

* * * * *